US009429012B2

(12) United States Patent
Ahmad et al.

(10) Patent No.: US 9,429,012 B2
(45) Date of Patent: Aug. 30, 2016

(54) DOWNHOLE SALINITY MEASUREMENT

(71) Applicant: Saudi Arabian Oil Company, Dhahran (SA)

(72) Inventors: Talha Jamal Ahmad, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 521 days.

(21) Appl. No.: 13/888,779

(22) Filed: May 7, 2013

(65) Prior Publication Data
US 2014/0333307 A1    Nov. 13, 2014

(51) Int. Cl.
E21B 49/08    (2006.01)
G01V 3/18    (2006.01)
G01N 33/28    (2006.01)
E21B 47/10    (2012.01)
G01V 3/20    (2006.01)

(52) U.S. Cl.
CPC .............. *E21B 49/08* (2013.01); *E21B 47/102* (2013.01); *E21B 2049/085* (2013.01); *G01N 33/2823* (2013.01); *G01V 3/18* (2013.01); *G01V 3/20* (2013.01)

(58) Field of Classification Search
CPC .................................. G01V 3/18; G01V 3/20
USPC ......................................................... 324/324
See application file for complete search history.

(56) References Cited

U.S. PATENT DOCUMENTS

| | | | | |
|---|---|---|---|---|
| 2,669,873 A | * | 2/1954 | Gardner | G01F 1/372 310/11 |
| 2,733,201 A | | 1/1956 | Thompson | |
| 3,182,285 A | * | 5/1965 | Vogel | G01V 1/44 181/402 |
| 3,447,127 A | * | 5/1969 | Wiley | G01V 1/52 367/33 |
| 3,585,405 A | * | 6/1971 | Stettiner | B06B 1/0215 310/317 |
| 3,611,799 A | * | 10/1971 | Davis | E21B 49/10 175/50 |
| 3,685,158 A | * | 8/1972 | Planche | E21B 17/1021 33/302 |

(Continued)

OTHER PUBLICATIONS

Charles A. Goss, Deborah H. Charych, and Marcin Majda; Application of (3-Mercaptopropyl)trimethoxysliane as a Molecular Adhesive in the Fabrication of Vapor-Deposited Gold Electrodes on Glass Substrates; Analytical Chemistry, vol. 63, No. 1, Jan. 1, 1991 pp. 85-88.*

(Continued)

*Primary Examiner* — Jermele M Hollington
*Assistant Examiner* — Christopher McAndrew
(74) *Attorney, Agent, or Firm* — Bracewell LLP; Constance G. Rhebergen; Albert B. Kimball, Jr.

(57) ABSTRACT

A downhole salinity measurement and logging sensor system has multiple cells, each to measure conductivity, temperature and pressure of fluids at depths of interest in a wellbore. The multiple cells protect against effects of non-homogeneous wellbore fluids. The system also determines salinity of the liquid in the wellbore from conductance measurements, and stores the salinity data along with the temperature and pressure readings from the well. The sensors of conductivity, temperature and pressure are made using micro-fabrication technologies, and the system is packaged to comply with harsh downhole environments. The system may be deployed in the well with coiled tubing (CT), wireline or vehicles with a robotic system. The system can be deployed with an onboard memory, or with wireline surface access for real time access to measurement data or programming the device.

28 Claims, 5 Drawing Sheets

(56) References Cited

U.S. PATENT DOCUMENTS

| | | | |
|---|---|---|---|
| 4,287,415 A * | 9/1981 | Arnold | E21B 47/1015 250/269.6 |
| 4,291,267 A * | 9/1981 | Bonnet | G01V 13/00 324/557 |
| 4,300,043 A * | 11/1981 | Robbins | G01V 5/10 250/262 |
| 4,359,687 A * | 11/1982 | Vinegar | G01V 3/38 324/362 |
| 4,754,839 A * | 7/1988 | Gold | E21B 47/101 181/102 |
| 4,808,931 A | 2/1989 | Ling | |
| 4,860,580 A * | 8/1989 | DuRocher | E21B 49/10 166/264 |
| 4,962,665 A * | 10/1990 | Savage | E21B 49/10 324/324 |
| 4,975,645 A * | 12/1990 | Lucas | E21B 47/102 324/324 |
| 5,453,693 A * | 9/1995 | Sinclair | G01V 3/30 324/324 |
| 5,483,164 A | 1/1996 | Moss et al. | |
| 6,404,204 B1 | 6/2002 | Farruggia et al. | |
| 6,964,301 B2 * | 11/2005 | Hill | E21B 49/10 166/100 |
| 7,100,689 B2 * | 9/2006 | Williams | E21B 47/011 166/264 |
| 7,129,704 B2 | 10/2006 | Delhomme et al. | |
| 7,225,881 B1 * | 6/2007 | Bushnell | E21B 23/14 166/241.5 |
| 7,259,566 B2 | 8/2007 | Broadbent et al. | |
| 7,484,563 B2 * | 2/2009 | Zazovsky | E21B 49/10 166/100 |
| 7,703,317 B2 * | 4/2010 | Goodwin | E21B 49/10 73/152.24 |
| 7,793,712 B2 * | 9/2010 | Yamate | E21B 47/00 166/254.2 |
| 7,845,219 B2 * | 12/2010 | Goodwin | E21B 49/10 73/152.24 |
| 8,109,157 B2 | 2/2012 | Kanayama et al. | |
| 2005/0077901 A1 | 4/2005 | Delhomme et al. | |
| 2008/0308271 A1 * | 12/2008 | Chouzenoux | E21B 47/01 166/250.02 |
| 2009/0033516 A1 | 2/2009 | Alteirac et al. | |
| 2009/0247428 A1 * | 10/2009 | Duncum | C09K 8/12 507/120 |
| 2010/0011853 A1 | 1/2010 | Anthony et al. | |
| 2010/0155061 A1 * | 6/2010 | Zazovsky | E21B 49/008 166/264 |
| 2010/0206063 A1 * | 8/2010 | Fujisawa | E21B 49/10 73/152.24 |
| 2011/0114385 A1 | 5/2011 | DiFoggio | |
| 2012/0021529 A1 | 1/2012 | Nachef et al. | |
| 2013/0002258 A1 * | 1/2013 | Ligneul | E21B 47/06 324/376 |
| 2013/0037263 A1 | 2/2013 | Cheung | |
| 2013/0066605 A1 * | 3/2013 | Li | E21B 49/06 703/2 |
| 2014/0238668 A1 * | 8/2014 | Bittleston | E21B 7/00 166/250.01 |
| 2014/0333307 A1 * | 11/2014 | Ahmad | E21B 49/08 324/324 |

OTHER PUBLICATIONS

Chaudhuri et al., "Design of a High Performance MEMS Pressure Sensor Array with Signal Conditioning Unit for Oceanographic Applications", Sensors & Transducers Journal, Nov. 2008, pp. 83-95, vol. 98, Issue 11, IFSA.

Fries et al., "Maskless Lithographic PCB/Laminate MEMS for a Salinity Sensing System", University of South Florida, College of Marine Sciences, Center for Ocean Technology *Electrical Engineering Dept., pp. 1-6.

Jonas Jonsson, "Microsystems Technology for Underwater Vehicle Applications" Digital Comprehensive Summaries of Uppsala Dissertations from the Faculty of Science and Technology 914, 2012, pp. 1-90, Uppsala Universitet.

Hyldgard et al., "Fish & Chips: Single Chip Silicon MEMS CTDL Salinity, Temperature, Pressure and Light Sensor for Use in Fisheries Research", 2005, pp. 303-306, IEEE.

International Search Report and Written Opinion for related PCT application PCT/US2014/036769 dated Jul. 13, 2015.

\* cited by examiner

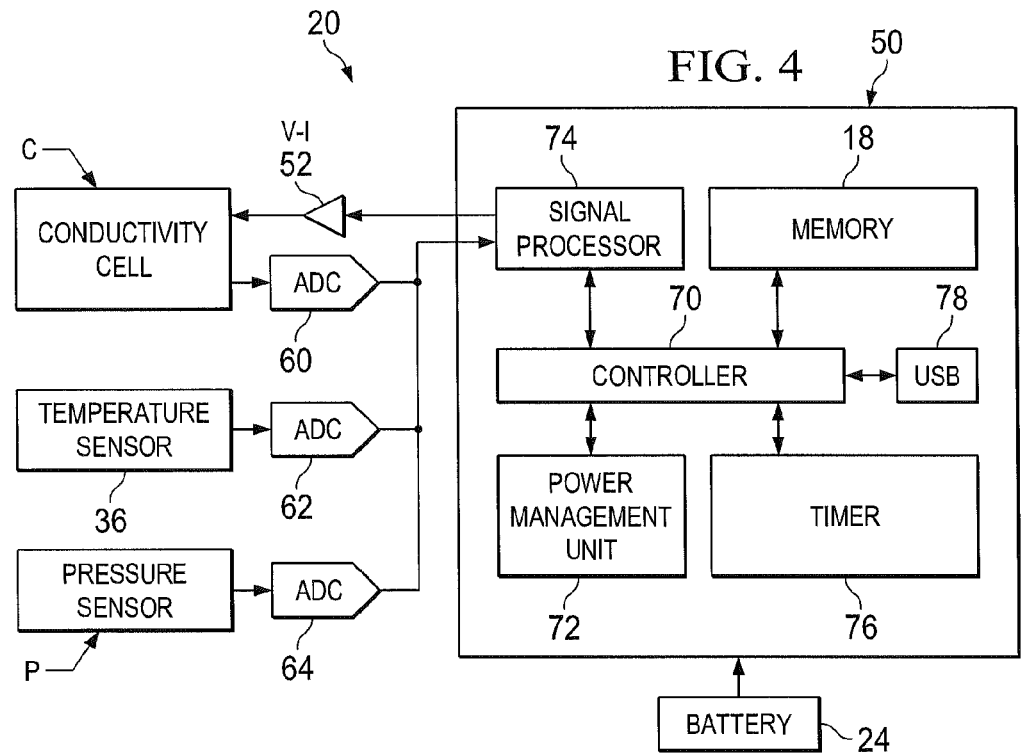
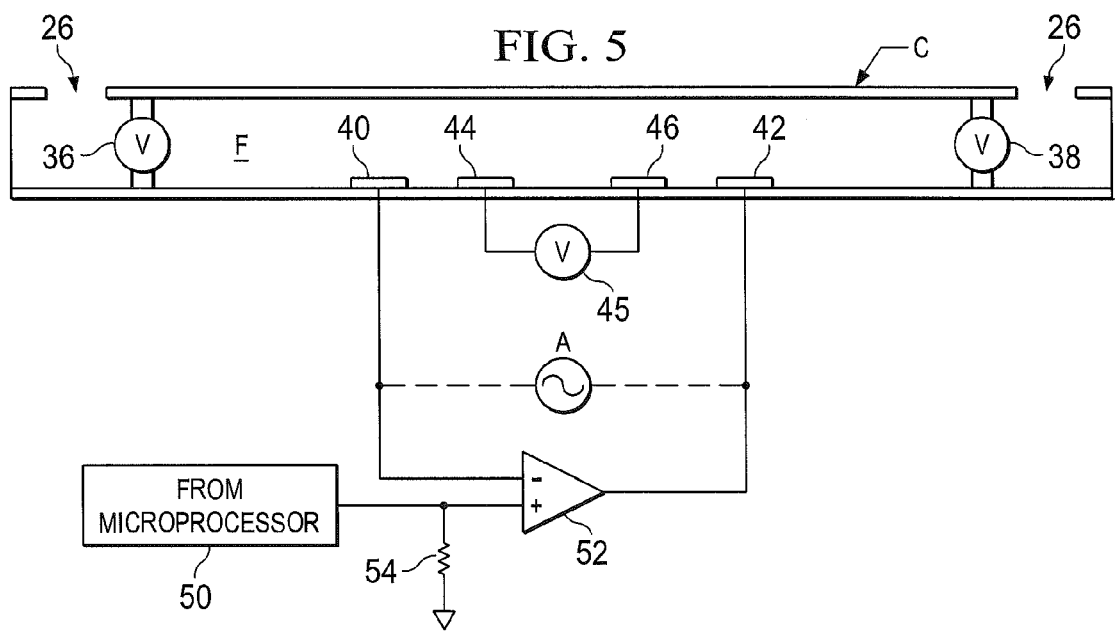

DOWNHOLE SALINITY MEASUREMENT

BACKGROUND OF THE INVENTION

1. Field of the Invention

The present invention relates to measurement and logging of salinity of fluids in well bores.

2. Description of the Related Art

Salinity measurement of fluid in a well borehole is important to evaluate the formation fluid. Salinity measurement can help in delineating oil and water and to estimate the moveable oil in a reservoir. Measurement of salinity as a function of well depth helps in differentiating between fresh and saline water and can help in identifying invasion of salt water into a producing borehole.

The downhole fluid environment is complex with presence of multiple non-homogenous phases with variable velocities. Measurement of a particular fluid characteristic performed at a single point in the wellbore might not represent an accurate representation of actual borehole fluid salinity.

So far as is known, downhole salinity measurement methods have in the past primarily been based on acoustic wave propagation through the formation fluid. Examples are U.S. Pat. No. 4,754,839 and U.S. Published Patent Application No. 2011/0114385.

U.S. Pat. No. 7,129,704 related to electromagnetic detection of progression of salt water fronts headed through formations to a water well. The increase of salt water in the formation before intrusion into the well water was measured with widely spaced electrodes since a significant portion of the induced electromagnetic field was required to pass through formation water outside the well bore.

SUMMARY OF THE INVENTION

Briefly, the present invention provides a new and improved apparatus for measuring salinity of fluid in a well bore. The apparatus includes a sonde for moving in the well bore to a depth of interest to receive well bore fluid. The sonde has a fluid sample chamber with fluid ports formed in it for entry of a well bore fluid sample volume. The apparatus includes at least one fluid conductivity sensor measuring conductivity parameters of the fluid sample volume in the sample chamber, and a data processor mounted in the sonde to determine salinity of the sample volume of well bore fluid at the depth of interest based on the measured conductivity parameters of the fluid in the sample chamber.

The present invention further provides a new and improved method of measuring salinity of fluid in a well bore at a depth of interest. A sonde is moved in the well bore to a depth of interest, and a sample volume of fluid from the well bore is admitted into a sample chamber in the sonde. A measure of the conductivity of the fluid sample in the sample chamber, and the salinity of the fluid sample is determined based on the formed measure of conductivity of the fluid sample in the sample chamber.

BRIEF DESCRIPTION OF THE DRAWINGS

FIG. 4 is a schematic electrical circuit diagram of the borehole fluid salinity measurement tool according to the present invention.

FIG. 5 is a schematic electrical circuit diagram of a conductivity measuring cell of the borehole fluid salinity measurement tool according to the present invention.

DETAILED DESCRIPTION OF THE PREFERRED EMBODIMENTS

Figure 1:
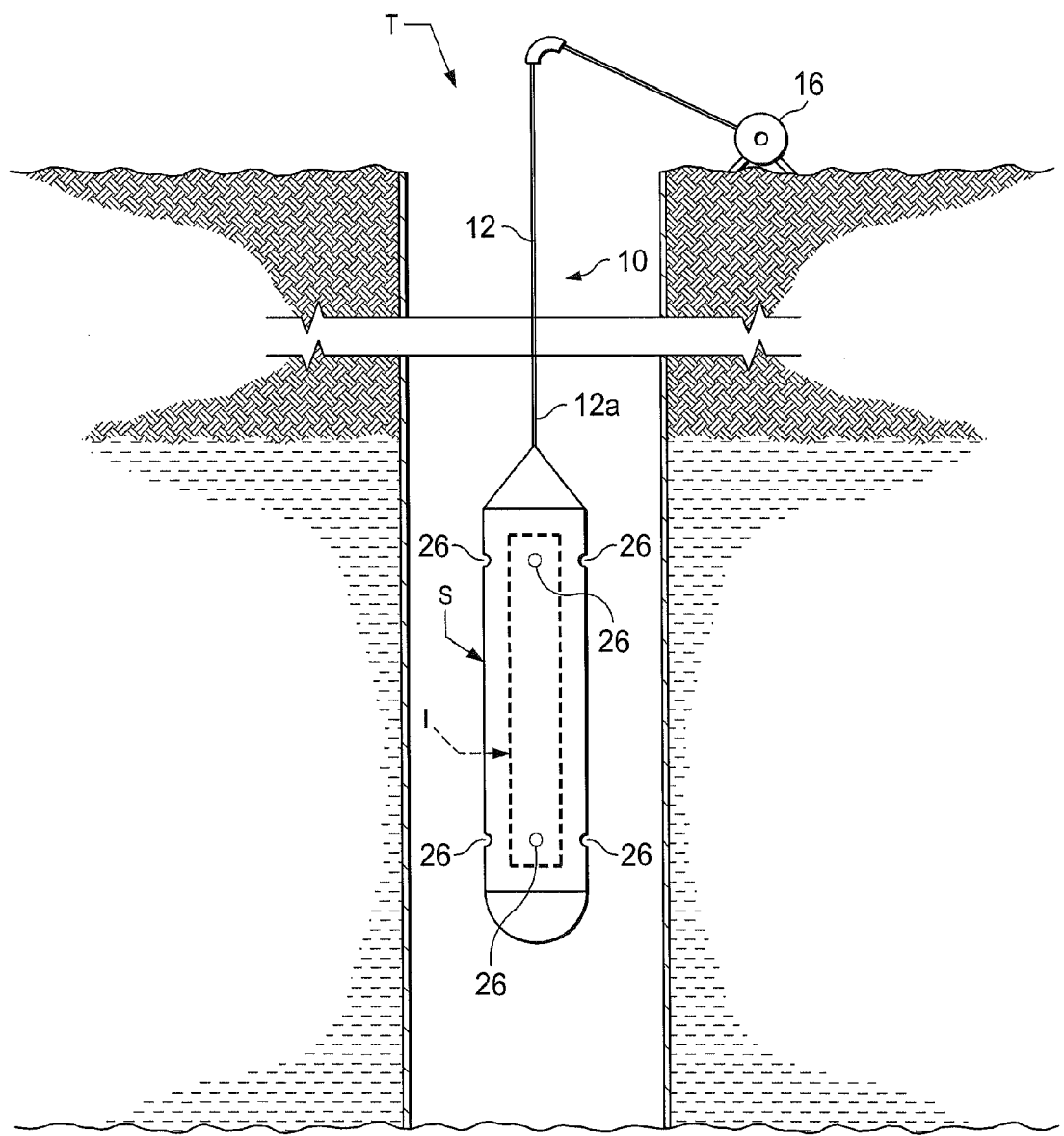
FIG. 1 is a view taken partly in cross-section of a borehole fluid salinity measurement tool according to the present invention deployed on coiled tubing in a wellbore.

In the drawings, a downhole salinity measuring tool or apparatus T is shown (FIG. 1) deployed in a wellbore or borehole 10. The downhole salinity measuring tool T includes a plurality of conductivity cells C (FIGS. 2 and 5) deployed in a sonde S which is deployed in the well bore 10, which may be a wet production hydrocarbon well or a water well. The borehole 10 may be either an uncased open hole or cased hole with well casing installed. The sonde S may be deployed on a lower end of coiled tubing 12 as shown in FIG. 1 or on a signal conducting wireline or e-line 14 (FIG. 7) as will be described.

The sonde S of FIG. 1 is suitably attached to a lower end 12a of the coiled tubing 12 by clamping or other suitable connection arrangement. The coiled tubing 12 is injected into the borehole 10 from a storage reel 16 to lower the sonde S to selected depths of interest in the well bore 10 so that fluid salinity of fluid at those depths may be measured and recorded. The depth of the sonde in the well 10 is measured and recorded based on data readings of the length of coiled tubing 12 injected into the well.

As the sonde S is lowered in the well 10, sample volumes of the well bore fluid at elected depths of interest are taken by the tool T in the conductivity cells C. As will be set forth, the salinity of the borehole fluid at a depth of interest is determined based on the conductivity measurements from the cells C, and the determined salinity value(s) of the borehole fluid at such depths measured and recorded or stored as data for analysis and evaluation. Measures of the temperature and pressure of the fluid samples are also obtained by instrumentation in the sonde S, as will be set forth. The fluid samples in the cells are then allowed to flow from the cells as the sonde S moves to a new well depth for another fluid sample.

By obtaining fluid samples and determining salinity, temperature and pressure at a number of selected depths of interest, a number of well fluid sampling and salinity measurements are obtained with a pre-programmed measurement schedule or plan over formations or depths of interest in the well 10. Measured data obtained in the coiled tubing deployed sonde S of FIG. 1 is stored in on-system memory 18 of instrumentation components 20 contained in an instrumentation cartridge I (FIGS. 1, 2 and 7) of the sonde S. Operating power for the instrumentation 20 of the sonde S is provided by an on-system battery 24 in the instrumentation cartridge I. The measured salinity, temperature and pressure data obtained at the various depths in the well 10 and stored in on-board memory 18 are transferred to a conventional computer for analysis, further processing and display after the tool T returns from the well 10.

Figure 2:
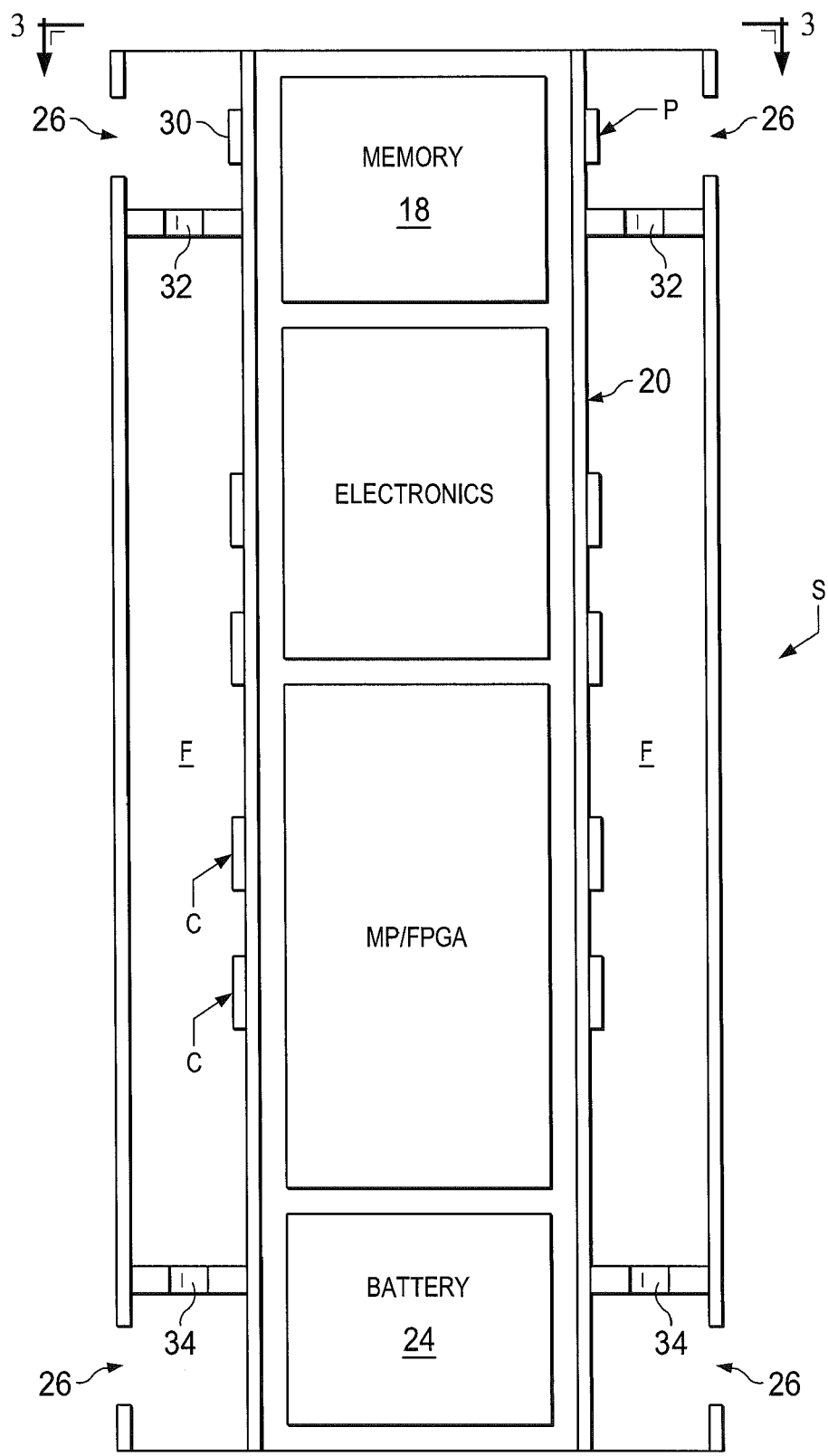
FIG. 2 is an enlarged vertical cross-sectional view of structure of the borehole fluid salinity measurement tool according to the present invention.
Figure 3:
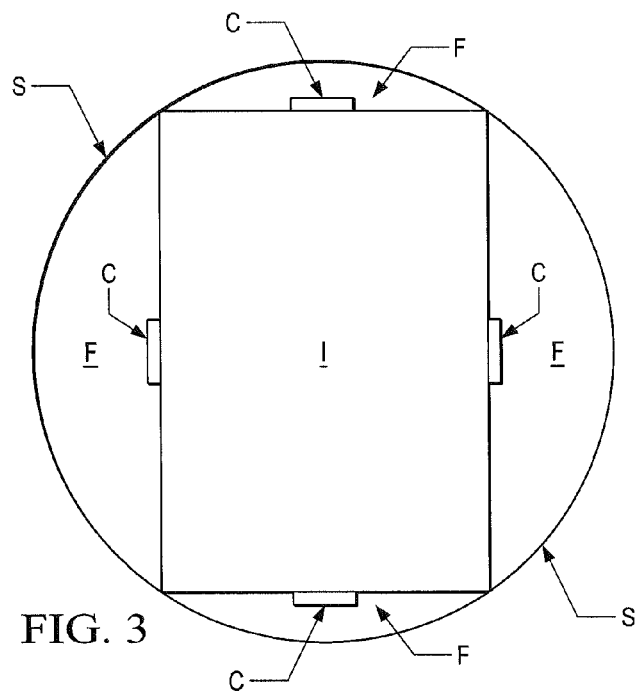
FIG. 3 is a horizontal cross-sectional view taken along the lines 3-3 of FIG. 2.

A salinity measurement performed based on a single measurement in a wellbore might not give an accurate value of fluid salinity because of the non-homogeneity of the wellbore fluid and the presence of multiphase flow regimes. Accordingly, with the present invention, to avoid the effect of possible wellbore fluid non-homogeneity and multiphase flow, as well as to improve accuracy of measurement, the tool T contains four conductivity cells C mounted at a common elevation on the instrumentation cartridge I within the sonde S as shown in FIGS. 2 and 3. A suitable number of fluid passage ports 26 are formed in the body of sonde S to allow well bore fluid presence and containment with the interior of the sonde S.

The well bore fluid sample in each conductivity cell C is received in a fluid sample chamber F (FIGS. 2 and 5). The shape, size and volume of the chamber F defines the geometry of the conductivity cell C. The sonde S also preferably includes a fluid temperature sensor 30 measuring temperature of the sample volume of well bore fluid in the fluid sample chamber, and a fluid pressure sensor P measuring pressure of the sample volume of well bore fluid in the fluid sample chamber.

FIG. 5 is a cross-sectional view of a single conductivity cell C along with a schematic view of associated electronics. Each cell C includes fluid receiving channel or chamber F located between a fluid inlet port 32 (FIG. 2) and a fluid outlet port 34 for wellbore liquids for passage of wellbore fluid from the interior of the sonde S. As shown schematically in FIG. 5, the chamber or channel F can be selectively opened and closed for entry and exit of well bore fluid by digitally controlled check valves 36 and 38 in inlet and outlet ports 32 and 34, respectively to obtain sample volumes of the wellbore fluid. The valves 36 and 38 are preferably operated by solenoids or other suitable valve actuators.

Each conductivity cell C includes electrodes located within fluid chamber F. Two drive electrodes 40 and 42 apply alternating current (AC) to the wellbore fluid in the chamber F. Preferably a high frequency alternating current is applied between the drive electrodes 40 and 42 as indicated by the instrumentation 20. The high frequency is used to avoid corrosion. In a preferred embodiment 10 KHz is used, although frequencies in a range of from 1 KHz to 100 KHz could be used.

Sense electrodes 44 and 46 form a measure of the voltage difference between spaced positions in the chamber F in response to the current between drive electrodes 40 and 42. The electrodes 40, 42, 44 and 46 are preferably fabricated using platinum on a glass chip with an insulative plastic or synthetic resin used as the body of conductivity cell C housing the chamber F.

The conductivity of the wellbore fluid sample in the chamber F of each conductivity cell C is determined based on the product of the determined measure of liquid conductance (G) of the sample volume of well fluid in the cell, and cell constant ($\sigma$) which is a constant which is defined by the geometry and dimensions of the sample chamber. The conductance value G is the reciprocal of a measured fluid resistance (R) of the sample volume obtained based on the current and voltage measured with the drive electrodes 40 and 42 and the sense electrodes 44 and 46. The fluid resistance R is determined using Ohm's law R=V/I relationship measured as indicated schematically at 45 of the voltage difference V between the sense electrodes 44 and 46 for an applied current level I applied by and flowing between the drive electrodes 40 and 42.

The high frequency alternating current wave signal between drive electrodes is generated under control from microprocessor 50 (FIG. 4) of the instrumentation 20. The signal so generated is converted to a current signal in an operational amplifier 52 (FIG. 5), and a resistor 54. The amplitude of sine wave voltage signal from operational amplifier 52 is preferably limited to an acceptable low level such as 1V to avoid electrolysis and metal corrosion, as the borehole fluid sample could be brine with high saturation of salts. It should be understood that low voltage levels in the range of less than 2 volts may be used.

Based on the resistance R obtained from the conductance and the cell constant $\sigma$ based on the physical geometry of cell C, resistivity of the borehole fluid sample is thus determined. The determined wellbore fluid sample resistivity is representative of the salinity of the borehole fluid sample in the each conductivity cell C. The conductivity measurements are obtained in each of the cells C and an average of these values is determined and stored as the representative salinity of the wellbore fluid at the sample depth of interest.

The temperature sensor 30 is usually a thermal resistive device with a linear resistance-to-temperature relationship for temperature measurement. Resistance (R) of a thermal resistive device depends on the material's resistivity ($\rho$), the structure's length (L) and cross section area (A):

$$R=\rho L/A$$

The change in temperature can be calculated by measuring the change in resistance by the following formula using initial values of resistance and temperature, $R_o$ and $T_o$ and the temperature coefficient ($\alpha$):

$$R=R_o(1+\alpha(T-T_o))$$

A platinum resistance thermometer (PRT) is preferably used as the temperature sensor 30. Platinum has a higher temperature range, good stability and low tendency to react with surrounding material as required for downhole conditions. These unique properties of platinum enable PRT to operate in temperature range of $-272.5°$ C. to $961.78°$ C. The platinum resistor of temperature sensor 30 is typically fabricated on a glass substrate.

The pressure sensor P which determines fluid pressure in the well is preferably a piezoresistive pressure sensor made using micro electro-mechanical systems (MEMS) fabrication techniques. The pressure sensor P thus preferably takes the form of a membrane over a cavity. In such a pressure sensor, the magnitude of membrane movement corresponds to the pressure level imposed by the wellbore fluid on the membrane. Changes in pressure on the membrane change the stress in membrane which can be measured by a change in resistance.

The conductivity cells C, the temperature sensor 30, and the pressure sensor P each form analog signal measures indicative of the value of the boreholes fluid parameter measures sensed. The analog signals from the borehole sensors are converted in analog-to-digital converters 60, 62 and 64, respectively, into suitable digital format for data acquisition and storage in on-system memory 18 and for processing by the microprocessor 50.

The salinity of the well bore fluid sample is determined in the on-board microprocessor 50 of the instrumentation 20 based on liquid conductivity, as described above, and stored in on-board memory 18, along with measured temperature and pressure of the wellbore fluid. From the measured salinity, conductance, temperature and pressure obtained wit the tool T, other borehole fluid parameters can also be computed including resistivity, density, acoustic velocity, freezing point, specific heat and potential density.

The microprocessor 50 serves as the main processing unit in on-board instrumentation of the sonde S. The microprocessor 50 includes a main controller 70, a power management unit 72, a digital signal processer 74, a timer 76 and the on-board memory 18. The memory 18 serves as internal memory for the tool T. The amount of memory provided depends upon the wellbore fluid measurement interval, total measurement time and number of parameters to be stored for each measurement. If the measurement is to be done over a larger range of depths of interest or with small measurement intervals, an external random access memory can be included and interfaced with microprocessor 50.

The digital signal processor 74 performs signal processing tasks including generation of signals for conductivity testing and computation of liquid conductance, resistivity and salinity in the manner described above. The timer 76 determines the time of occurrence of and the time interval between obtaining borehole fluid measurements, and thus defines the measurement frequency. The controller 70 controls the other subsystems of the microprocessor 50 and performs the required synchronization. An USB interface 78 is provided for connection of the controller 70 to an external computer at the surface for programming of operations in the wellbore and for transfer of data from the memory 18.

Battery 24 which provides power for the microprocessor 50 and other electronics of the sonde S preferably is a rechargeable lithium ion battery. The power management unit 72 is implemented in the microprocessor 50 to efficiently manage the operating electrical power usage. A power optimized system architecture is utilized in the power management unit 72 in order to maximize the system service life. The functionality of the system is divided into different working states. The power management unit 72 activates modules required for the current working state and switches off the rest. Power saving strategies at both sensor level and system level are implemented to minimize power consumption of the system.

Detailed analysis and further measurements based on the borehole fluid data obtained S can be performed after the sonde S is moved out of the well bore to the surface. The contents of memory 18 are transferred by connecting the microprocessor 50 with a computer at the surface and retrieving the data.

Figure 6:
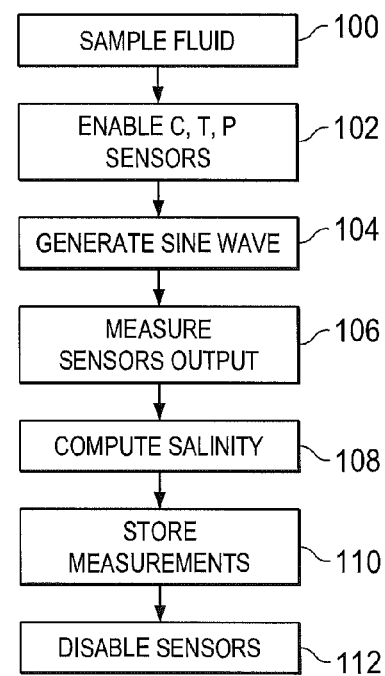
FIG. 6 is a functional block diagram of the procedure for measuring borehole fluid salinity according to the present invention.

FIG. 6 illustrates the operating sequence of measuring salinity of borehole fluid according to the present invention. The sonde S is deployed in the well bore with coiled tubing 12. At a pre-programmed time to allow the sonde to reach a depth of interest, the valves of the conductivity cells C are activated to sample the wellbore fluid as indicated at step 100. The sensors of the conductivity cells C are activated by the microprocessor 50 as indicated at step 102 so that borehole fluid salinity can be determined at the depth of interest.

During step 104, the alternating current signal is applied to the borehole fluid samples in the conductivity cells C by current flow between the drive electrodes 40 and 42. The resultant voltage is concurrently sensed by the sense electrodes 44 and 46 as indicated by step 106. Pressure and temperature measures of the wellbore fluid are also obtained from pressure sensor P and temperature sensor 30 in step 106. The measured borehole fluid data after collection is then collected and processed by the microprocessor 50 to determine borehole fluid salinity, as indicated by step 108.

The computed salinity and other measurements of borehole fluid data are stored in the memory 18 during step 110, along with a time stamp or record of the time the sample was taken. The sensors in the sonde S are then disabled during step 112. Movement of the sonde S in the well bore continues and at the next pre-programmed time indicated by the timer 76, the foregoing sequence is repeated.

The well bore fluid parameter sensors of the sonde S are preferably fabricated with micro electro-mechanical fabricated or MEMS microfabrication technologies which offer miniaturization as well as accurate measurement. The analog-to-digital converters 60, 62 and 64, the microprocessor 50 and other electronic components used as instrumentation 20 in the sonde S may be commercial, off the shelf harsh environment electronic components. A harsh environment commercial electronics component line is provided by Texas Instruments which can operate in the temperature range of −55° C. to 210° C.

Alternatively, a custom made application specific integrated chip or ASIC may be utilized, with multilayer thick film fabrication or silicon-on-insulator techniques and ceramic packaging. The board for the electronics of the sonde S is preferably a high temperature printed circuit board with an inorganic ceramic substrate. The board and electronics have ceramic packaging and are hermetically sealed to protect the circuits from well fluids.

Figure 7:
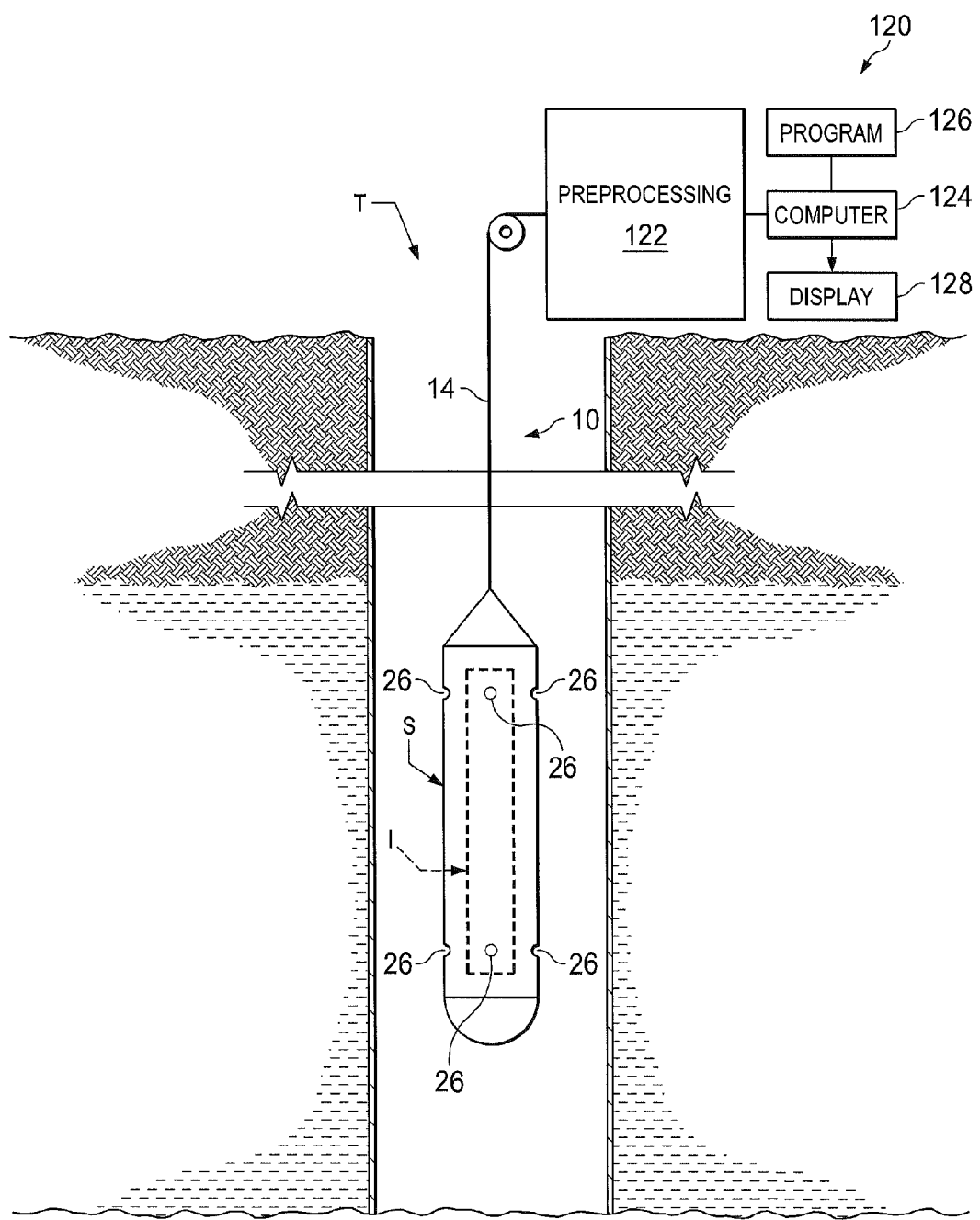
FIG. 7 is a view taken partly in cross-section of a borehole fluid salinity measurement tool according to the present invention deployed on a wireline in a wellbore.

As described above, the sonde S can also be deployed using the e-line or signal conducting wireline 14 (FIG. 7). In this case, the wireline 14 is connected to a computer system 120 at the surface. The components of the sonde S in FIG. 7 to obtain measures of borehole fluid salinity, temperature and pressure are of like structure and functionality to those described for the coiled tubing deployed sonde S of FIG. 1.

Borehole fluid data from the sonde S are received and recorded as functions of borehole depth in memory of uphole telemetry and preprocessing circuitry 122. A surface processor computer 124 receives and processes the borehole fluid data of interest under control of stored program instructions stored as indicated at 126. The results from processing by the processor computer 124 are available in real time during salinity measurement operations for analysis on a suitable display or plotter, such as display 128. A depth measurement system (not shown) also is present as a component of the wireline 14 to also correlate or indicate downhole wellbore fluid sensor measurements and parameters of interest to their respective depths or true locations within the borehole 10 at which such measurements are made.

The surface computer 124 can be a mainframe server or computer of any conventional type of suitable processing capacity such as those available from any of several sources. Other digital computers or processors may also be used, such as a laptop or notebook computer, or any other suitable processing apparatus both at the well site and a central office or facility.

A power cable or conductor in the wireline 14 is used to charge the battery 24 and borehole fluid parameters of interest measured by the tool T can be accessed at the surface by computer system 120 in real-time. Conventional wireline telemetry and control circuitry are included in the tool T of FIG. 7 for transfer of data over the wireline 14 to the surface for processing by processor computer 124 and to receive control signals for the tool T from the computer system 120. The controller 70 in the tool T can also be programmed while in the well by instruction signals sent by wireline to change the acquisition parameters including measurement frequency of sensors, total measurement time and other required parameters.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. An apparatus for measuring salinity of fluid in a well bore comprising:
   (a) a sonde body for moving in the well bore to a depth of interest, the sonde body receiving well bore fluid therein;
   (b) the sonde body having a fluid sample chamber therein and a conductivity cell mounted in the fluid sample chamber;
   (c) the sonde body further having a plurality of fluid passage ports formed therein to allow well bore fluid presence and containment in an interior portion of the sonde to obtain sample volumes of the well bore fluid;
   (d) the fluid sample chamber having fluid ports for passage of well bore fluids from the interior portions of the sonde body into the fluid sample chamber;
   (e) at least one fluid conductivity sensor mounted in the fluid sample chamber and measuring conductivity parameters of the well bore fluid sample volume in the sample chamber; and
   (f) a data processor mounted in the sonde and determining salinity of the sample volume of well bore fluid at the depth of interest based on the measured conductivity parameters of the well bore fluid in the sample chamber.

2. The apparatus of claim 1, wherein the conductivity sensor comprises:
   at least two drive electrodes mounted in the fluid sample chamber at spaced locations from each other.

3. The apparatus of claim 2, further including a source of alternating current applying a specified level of alternating current power to the drive electrodes to pass through the fluid sample volume in the sample chamber.

4. The apparatus of claim 3, further including an instrumentation cartridge mounted in the sonde, the instrumentation package containing the source of alternating current.

5. The apparatus of claim 2, wherein the drive electrodes are each metallic electrodes formed on glass substrates.

6. The apparatus of claim 2, wherein the conductivity sensor comprises:
   at least two sense electrodes mounted in the fluid sample chamber at spaced locations from each other.

7. The apparatus of claim 6, further including a voltage measuring meter sensing the voltage between the sense electrodes as alternating current passes through fluid sample volume in the sample chamber.

8. The apparatus of claim 7, wherein the data processor receives the sensed voltage and determines conductivity based of the sensed voltage and the specified level of alternating current power.

9. The apparatus of claim 1, further including:
   a fluid temperature sensor measuring temperature of the sample volume of well bore fluid in the fluid sample chamber.

10. The apparatus of claim 1, further including:
    a fluid pressure sensor measuring pressure of the sample volume of well bore fluid in the fluid sample chamber.

11. The apparatus of claim 1, wherein the data processor is mounted in an instrumentation cartridge in the fluid sample chamber in the sonde.

12. The apparatus of claim 2, wherein the at least one conductivity sensor is mounted with the instrumentation cartridge.

13. The apparatus of claim 1, further including a plurality of conductivity sensors measuring conductivity of the sample volume of well bore fluid in the sample chamber.

14. The apparatus of claim 1, wherein the data processor is mounted in an instrumentation cartridge in the fluid sample chamber in the sonde and wherein the plurality of conductivity sensors are mounted in conductivity cells with the instrumentation cartridge at a common elevation about the instrumentation cartridge.

15. The apparatus of claim 1, further including fluid inlet control valves mounted in the fluid ports in the fluid sample chamber sonde controlling passage between the fluid sample chamber and the well bore.

16. The apparatus of claim 1, wherein the sonde is mounted with coiled tubing for moving in well bore to the depth of interest.

17. The apparatus of claim 2, further including data storage media mounted with the data processor in the sonde.

18. The apparatus of claim 1, wherein the sonde is mounted with a signal conducting wire line for moving in well bore to the depth of interest.

19. The apparatus of claim 9, further including a data transmitter sending the determined salinity of the sample volume of well bore fluid at the depth of interest over the wire line for logging of the well.

20. A method of measuring salinity of fluid in a well bore at a depth of interest with a sonde body for being lowered in the well to the depth of interest, and having a sonde body with a fluid sample chamber and fluid passage ports formed therein, comprising the steps of:
    (a) moving the sonde body in the well bore to a depth of interest;
    (b) admitting well bore fluid passage into an interior portion of the sonde body or fluid presence and containment;
    (c) admitting a sample volume of well bore fluid from the interior of the sonde body through the fluid passage ports into the fluid sample chamber in the sonde body;
    (c) forming a measure of the conductivity of the well bore fluid sample in the fluid sample chamber; and
    (d) determining the salinity of the well bore fluid sample based on the formed measure of conductivity of the well bore fluid sample in the fluid sample chamber.

21. The method of claim 20, wherein the step of determining salinity includes the step of:
    applying a specified level of alternating current power to pass between spaced positions in the sample chamber through the fluid sample volume in the sample chamber.

22. The method of claim 21, wherein the step of determining salinity includes the step of:
    sensing the voltage between spaced positions in the sample chamber as the alternating current passes through fluid sample volume in the sample chamber.

23. The method of claim 20, wherein the step of moving comprises:
    moving the sonde to the depth of interest with coiled tubing.

24. The method of claim 23, further including the step of:
   storing the determined salinity of the fluid sample in data memory.

25. The method of claim 20, wherein the step of moving comprises:
   moving the sonde to the depth of interest with a signal conducting wire line.

26. The method of claim 25, further including the step of:
   transmitting the determined salinity of the fluid sample over the wire line for logging of the well.

27. The method of claim 20, further including the step of:
   forming a measure of the temperature of the fluid sample in the sample chamber.

28. The method of claim 20, further including the step of:
   forming a measure of the pressure of the fluid sample in the sample chamber.

* * * * *